United States Patent
An et al.

(10) Patent No.: US 11,834,419 B2
(45) Date of Patent: Dec. 5, 2023

(54) COMPOUND, PHOTORESIST COMPOSITION COMPRISING SAME, PHOTORESIST PATTERN COMPRISING SAME, AND METHOD FOR MANUFACTURING PHOTORESIST PATTERN

(71) Applicant: LG CHEM, LTD., Seoul (KR)

(72) Inventors: Junhyun An, Daejeon (KR); Minyoung Lim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 676 days.

(21) Appl. No.: 17/046,095

(22) PCT Filed: Oct. 11, 2019

(86) PCT No.: PCT/KR2019/013365
§ 371 (c)(1),
(2) Date: Oct. 8, 2020

(87) PCT Pub. No.: WO2020/076123
PCT Pub. Date: Apr. 16, 2020

(65) Prior Publication Data
US 2021/0032208 A1 Feb. 4, 2021

(30) Foreign Application Priority Data

Oct. 11, 2018 (KR) .................. 10-2018-0120978

(51) Int. Cl.
| C07D 237/26 | (2006.01) |
| C07C 381/12 | (2006.01) |
| G03F 7/004 | (2006.01) |
| C08F 220/28 | (2006.01) |
| C08F 232/08 | (2006.01) |
| G03F 7/033 | (2006.01) |

(52) U.S. Cl.
CPC .......... *C07D 237/26* (2013.01); *C07C 381/12* (2013.01); *C08F 220/281* (2020.02); *C08F 232/08* (2013.01); *G03F 7/0045* (2013.01); *G03F 7/033* (2013.01)

(58) Field of Classification Search
CPC ..................... C07D 237/26; C07C 381/12
See application file for complete search history.

(56) References Cited

U.S. PATENT DOCUMENTS

| 7,527,912 | B2 | 5/2009 | Ohsawa et al. | |
| 8,900,797 | B2 | 12/2014 | Nakasugi et al. | |
| 8,932,795 | B2 | 1/2015 | Seshimo et al. | |
| 9,323,146 | B2 | 4/2016 | Namai et al. | |
| 9,411,225 | B2 | 8/2016 | Ohashi et al. | |
| 9,921,475 | B1 | 3/2018 | Agad et al. | |
| 10,018,911 | B2 * | 7/2018 | Nakagawa | G03F 7/168 |
| 11,281,100 | B2 * | 3/2022 | Nishikori | G03F 7/0045 |
| 11,609,495 | B2 * | 3/2023 | Nishikori | G03F 7/0046 |
| 2008/0085469 | A1 * | 4/2008 | Ohsawa | C07D 491/18 548/530 |
| 2011/0200935 | A1 * | 8/2011 | Masuyama | C07D 215/58 548/542 |
| 2011/0201823 | A1 * | 8/2011 | Yoshida | G03F 7/0045 548/334.1 |
| 2012/0122032 | A1 * | 5/2012 | Anryu | C07D 327/06 549/13 |
| 2012/0237874 | A1 * | 9/2012 | Yamaguchi | C07D 307/93 544/5 |
| 2013/0171567 | A1 * | 7/2013 | Aqad | G03F 7/0392 430/285.1 |
| 2015/0212408 | A1 * | 7/2015 | Masuyama | G03F 7/0045 430/281.1 |
| 2018/0088464 | A1 * | 3/2018 | Fujiwara | C07D 409/10 |
| 2018/0275516 | A1 * | 9/2018 | Fujiwara | C07D 335/02 |
| 2019/0243244 | A1 | 8/2019 | Kaneko et al. | |

FOREIGN PATENT DOCUMENTS

| CN | 102781911 A | 11/2012 | |
| JP | 2008-106045 A | 5/2008 | |
| JP | 2012046501 A * | 3/2012 | .......... C07C 309/14 |
| JP | 2013-092618 A | 5/2013 | |
| KR | 10-1035742 B1 | 5/2011 | |
| KR | 10-2011-0127601 A | 11/2011 | |
| KR | 2012023530 A * | 3/2012 | .......... C07C 309/14 |
| KR | 10-2014-0139511 A | 12/2014 | |
| KR | 10-2016-0004964 A | 1/2016 | |
| KR | 10-1673890 B1 | 11/2016 | |
| KR | 10-1813298 B1 | 12/2017 | |
| KR | 10-2018-0025216 A | 3/2018 | |
| WO | 2018-070327 A1 | 4/2018 | |

OTHER PUBLICATIONS

International Search Report issued for International Application No. PCT/KR2019/013365 dated Jan. 15, 2020, 5 pages.
Knall et al., "A trifunctional linker suitable for conducting three orthogonal click chemistries in one pot," Org. Biomol. Chem., (2016) vol. 14, pp. 10576-10580.

* cited by examiner

*Primary Examiner* — Amanda C. Walke
(74) *Attorney, Agent, or Firm* — ROTHWELL, FIGG, ERNST & MANBECK, P.C.

(57) ABSTRACT

A compound represented by Chemical Formula 1, a photoresist composition comprising the same, a photoresist pattern comprising the same, and a method for preparing a photoresist pattern

[Chemical Formula 1]

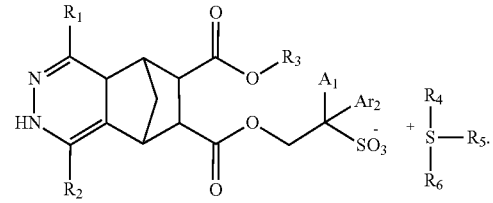

16 Claims, No Drawings

COMPOUND, PHOTORESIST COMPOSITION COMPRISING SAME, PHOTORESIST PATTERN COMPRISING SAME, AND METHOD FOR MANUFACTURING PHOTORESIST PATTERN

TECHNICAL FIELD

This application is a 35 U.S.C. 371 National Phase Entry Application from PCT/KR2019/013365 filed on Oct. 11, 2019, designating the United States, which claims priority to and the benefits of Korean Patent Application No. 10-2018-0120978, filed with the Korean Intellectual Property Office on Oct. 11, 2018, the entire contents of which are incorporated herein by reference. The present specification relates to a compound, a photoresist composition comprising the same, a photoresist pattern comprising the same, and a method for preparing a photoresist pattern.

BACKGROUND OF THE INVENTION

A photoresist composition is used in, for example, a process of a microelectronic device for manufacturing small electronic components when manufacturing computer chips and integrated circuits. A process of a microelectronic device using a substrate material such as a silicon-based wafer used for manufacturing an integrated circuit is generally as follows.

A photoresist layer of a thin coating film is formed on a substrate using a photoresist composition or a photoresist film, and then the result is baked to fix the coating film on the substrate. The coating film fixed on the substrate is image-wise exposed to radiation. The exposed coating film is treated with a developing solution, and by dissolving and removing the exposed area or the unexposed area of the photoresist, a microelectronic device is formed.

High integration of a semiconductor has been advanced along with the development of photolithography technologies unmatched by other patterning techniques in terms of performance, reliability, and human and physical infrastructures.

Particularly, as a shorter light source and a matching photochemical reaction photoresist are used, the degree of device integration has rapidly increased with the development of KrF excimer laser (248 nm) and ArF laser (193 nm) lithography technologies using a high sensitivity chemical amplification-type photoresist.

Although 193i lithography technology has advanced to a level of progressing a process of manufacturing a device having a minimum line width of mid/late 10 nm through quadruple patterning, the process may not be generally used due to very high process costs and limited obtainable pattern shapes, and the resolution of 16 nm is recognized as a threshold. Extreme ultraviolet rays (EUV) have been predicted as an only technology capable of several nm patterning so far, however, the resolution of 12 nm is recognized as a threshold as well in this case due to an absence of a high resolution photoresist.

In view of the above, development of an extreme ultraviolet photoresist has been required for high integration of a semiconductor, however, some materials currently developed have problems to resolve such as improving sensitivity decrease, resolution and line width roughness (LWR).

BRIEF SUMMARY OF THE INVENTION

The present specification provides a compound, a photoresist composition comprising the same, a photoresist pattern comprising the same, and a method for preparing a photoresist pattern.

One embodiment of the present application provides a compound represented by the following Chemical Formula 1.

[Chemical Formula 1]

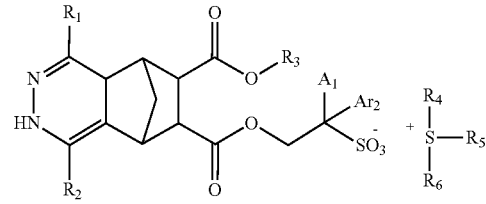

In Chemical Formula 1, $R_1$ and $R_2$ are the same as or different from each other, and each independently hydrogen; a halogen group; a nitrile group; a hydroxyl group; an ester group; a substituted or unsubstituted alkyl group; a substituted or unsubstituted aryl group; or a substituted or unsubstituted heteroaryl group, $R_3$ to $R_6$ are the same as or different from each other, and each independently hydrogen; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and $Ar_1$ and $Ar_2$ are the same as or different from each other, and each independently hydrogen; a halogen group; a substituted or unsubstituted alkyl group; or a substituted or unsubstituted aryl group.

Another embodiment of the present application provides a photoresist composition comprising a resin; the compound according to the present application; a photoacid generator (PAG); an acid diffusion control agent; and a quencher.

Another embodiment of the present application provides a photoresist pattern comprising the photoresist composition according to the present application.

Lastly, one embodiment of the present application provides a method for preparing a photoresist pattern, the method comprising forming a photoresist layer by coating the photoresist composition of the present application on a semiconductor substrate; selectively exposing the photoresist layer; and developing the exposed photoresist layer.

Advantageous Effects

A compound according to one embodiment of the present application is capable of, by comprising a structure of Chemical Formula 1, further enhancing contrast of an exposed portion and an unexposed portion in a photoresist process afterward, and is also capable of improving line width roughness (LWR) without reducing sensitivity.

In addition, the compound according to one embodiment of the present application comprises a photo-degradable base having the structure of Chemical Formula 1, and thereby has no sensitivity decrease caused by an increase in the base concentration of a photoresist pattern comprising the same, and is also capable of resolving a compatibility problem by changing substituents of Chemical Formula 1 depending on a resin included in a photoresist composition.

In addition, a photoresist composition comprising the compound according to the present application is capable of high resolution and freely forming pattern shapes by comprising the compound.

THE DETAILED DESCRIPTION OF THE INVENTION

Hereinafter, the present specification will be described in more detail.

In the present specification, a description of a certain part "including" certain constituents means capable of further comprising other constituents, and does not exclude other constituents unless particularly stated on the contrary.

Embodiments of the present disclosure will be described in detail with reference to accompanying drawings so that those skilled in the art may readily implement the present disclosure. However, the present disclosure may be embodied in various different forms, and is not limited to the embodiments described herein.

One embodiment of the present specification provides a compound represented by the following Chemical Formula 1.

[Chemical Formula 1]

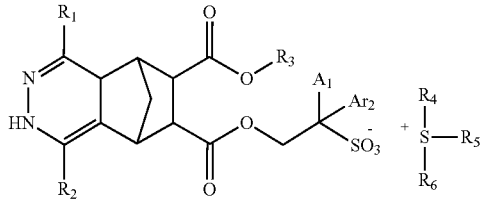

In Chemical Formula 1, $R_1$ and $R_2$ are the same as or different from each other, and each independently hydrogen; a halogen group; a nitrile group; a hydroxyl group; an ester group; a substituted or unsubstituted alkyl group; a substituted or unsubstituted aryl group; or a substituted or unsubstituted heteroaryl group, $R_3$ to $R_6$ are the same as or different from each other, and each independently hydrogen; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and $Ar_1$ and $Ar_2$ are the same as or different from each other, and each independently hydrogen; a halogen group; a substituted or unsubstituted alkyl group; or a substituted or unsubstituted aryl group.

The compound according to one embodiment of the present application is capable of, by comprising the structure of Chemical Formula 1, further enhancing contrast of an exposed portion and an unexposed portion in a photoresist process afterward, and is also capable of improving line width roughness (LWR) without reducing sensitivity.

In addition, the compound according to one embodiment of the present application comprises a photo-degradable base having the structure of Chemical Formula 1, and thereby has no sensitivity decrease caused by an increase in the base concentration of a photoresist pattern comprising the same, and is also capable of resolving a compatibility problem by changing substituents of Chemical Formula 1 depending on a resin included in a photoresist composition.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one, two or more substituents selected from the group consisting of a halogen group; a nitrile group; an imide group; an amide group; a carbonyl group; an ester group; a hydroxyl group; a carboxyl group (—COOH); a sulfonic acid group (—SO₃H); a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may comprise a biphenyl group. In other words, a biphenyl group may be an aryl group, or interpreted as a substituent linking two phenyl groups.

In the present specification,

means a site bonding to other substituents or bonding sites.

In the present specification, the halogen group may comprise fluorine, chlorine, bromine or iodine.

In the present specification, the number of carbon atoms of the imide group is not particularly limited, but is preferably from 1 to 30. Specifically, compounds having structures as below may be included, however, the imide group is not limited thereto.

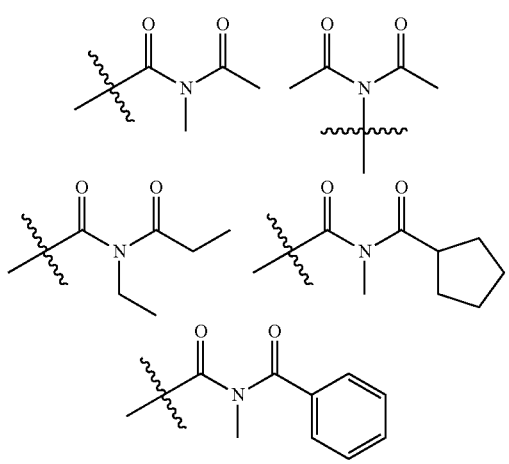

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, however, the amide group is not limited thereto.

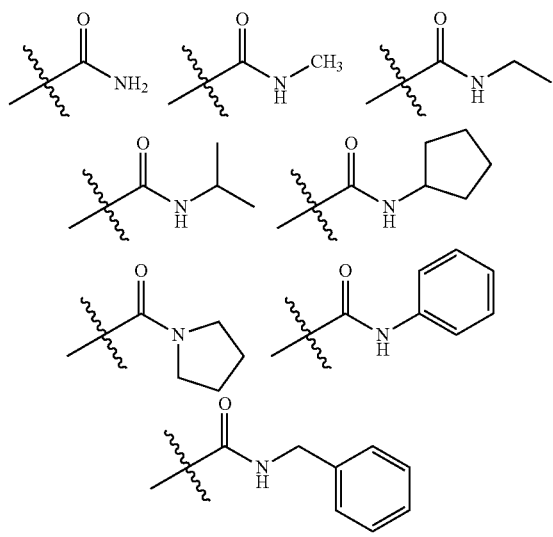

In the present specification, the number of carbon atoms of the carbonyl group is not particularly limited, but is preferably from 1 to 30. Specifically, compounds having structures as below may be included, however, the carbonyl group is not limited thereto.

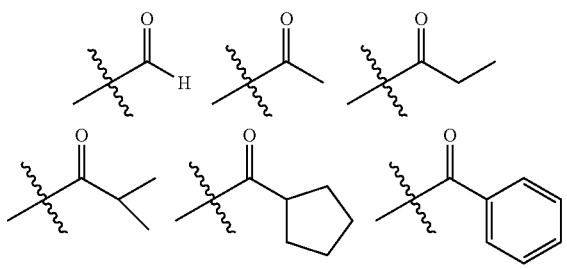

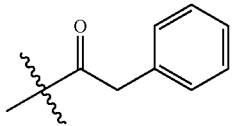

In the present specification, the ester group may be an alkyl ester group in which the oxygen of the ester group is substituted with a linear, branched or cyclic alkyl group having 1 to 25 carbon atoms; a cycloalkyl ester group in which the oxygen of the ester group is substituted with a monocyclic or polycyclic cycloalkyl group having 3 to 30 carbon atoms; or an aryl ester group in which the oxygen of the ester group is substituted with an aryl group having 6 to 30 carbon atoms. Specifically, compounds having the following structural formulae may be included, however, the ester group is not limited thereto.

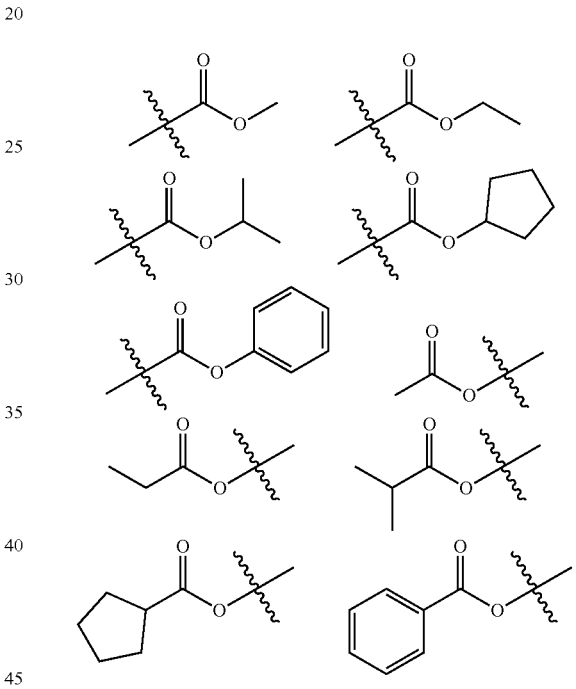

In the present specification, the alkyl group may be linear or branched, and although not particularly limited thereto, the number of carbon atoms is preferably from 1 to 30. Specific examples thereof may comprise methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the monoalkylamine group, the dialkylamine group, the N-alkylarylamine group, the alkylthioxy group, the alkylsulfoxy group and the N-alkylheteroarylamine group is the same as the examples of the alkyl group described above. Specifically, the alkylthioxy group may comprise a methylthioxy group, an ethylthioxy group, a tert-butylthioxy group, a hexylthioxy group, an octylthioxy group and the like, and the alkylsulfoxy group may comprise mesyl, an ethylsulfoxy group, a propylsulfoxy group, a butylsulfoxy group and the like, however, the alkylthoixy group and the alkylsulfoxy group are not limited thereto.

In the present specification, specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —BR$_{100}$R$_{101}$. R$_{100}$ and R$_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group may comprise a diphenylphosphine oxide group, a dinaphthylphosphine oxide group and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may comprise a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may comprise a naphthyl group, an anthracenyl group, a phenanthryl group, a triphenyl group, a pyrenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted, the following structures may be included, however, the structure is not limited thereto.

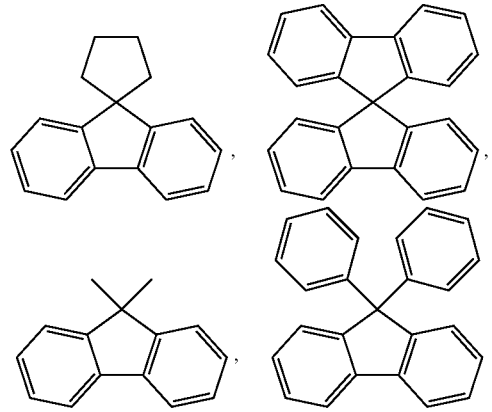

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the monoarylamine group, the diarylamine group, the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group may comprise a phenoxy group, a p-tolyloxy group, an m-tolyloxy group, a 3,5-dimethyl-phenoxy group, a 2,4, 6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like. Specific examples of the arylthioxy group may comprise a phenylthioxy group, a 2-methylphenylthioxy group, a 4-tert-butylphenylthioxy group and the like, and specific examples of the arylsulfoxy group may comprise a benzenesulfoxy group, a p-toluenesulfoxy group and the like. However, the aryloxy group, the arylthioxy group and the arylsulfoxy group are not limited thereto.

In the present specification, the heteroaryl group is a group comprising one or more atoms that are not carbon, that is, heteroatoms, and specifically, the heteroatom may comprise one or more atoms selected from the group consisting of O, N, Se, S and the like. The number of carbon atoms is not particularly limited, but is preferably from 2 to 30, and the heteroaryl group may be monocyclic or polycyclic. Examples of the heterocyclic group may comprise a thiophene group, a furanyl group, a pyrrole group, an imidazolyl group, a thiazolyl group, an oxazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzocarbazolyl group, a benzothiophene group, a dibenzothiophene group, a benzofuranyl group, a phenanthrolinyl group, an isoxazolyl group, an oxadiazolyl group, a thiadiazolyl group, a benzothiazolyl group, a phenothiazinyl group, a dibenzofuranyl group and the like, but are not limited thereto.

In the present specification, examples of the heteroaryl group in the monoheteroarylamine group, the diheteroarylamine group, the N-arylheteroarylamine group and the N-alkylheteroarylamine group are the same as the examples of the heteroaryl group described above.

In the present specification, the hydrocarbon ring may be aromatic, aliphatic or a fused ring of aromatic and aliphatic, and may be selected from among the examples of the cycloalkyl group or the aryl group except for those that are not monovalent.

In the present specification, the aromatic hydrocarbon ring may be monocyclic or polycyclic, and may be selected from among the examples of the aryl group except for those that are not monovalent.

In the present specification, the heteroring comprises one or more atoms that are not carbon, that is, heteroatoms, and specifically, the heteroatom may comprise one or more atoms selected from the group consisting of O, N, Se, S and the like. The heteroring may be monocyclic or polycyclic, may be aromatic, aliphatic or a fused ring of aromatic and aliphatic, and may be selected from among the examples of the heteroaryl group except for those that are not monovalent.

In one embodiment of the present application, $R_1$ and $R_2$ are the same as or different from each other, and may be each independently hydrogen; a halogen group; a nitrile group; a hydroxyl group; an ester group; a substituted or unsubstituted alkyl group; a substituted or unsubstituted aryl group; or a substituted or unsubstituted heteroaryl group.

In another embodiment, $R_1$ and $R_2$ are the same as or different from each other, and may be each independently hydrogen; a halogen group; an ester group; a substituted or unsubstituted $C_1$ to $C_{60}$ alkyl group; a substituted or unsubstituted $C_6$ to $C_{60}$ aryl group; or a substituted or unsubstituted $C_2$ to $C_{60}$ heteroaryl group.

In another embodiment, $R_1$ and $R_2$ are the same as or different from each other, and may be each independently hydrogen; a halogen group; an ester group; a substituted or unsubstituted $C_1$ to $C_{40}$ alkyl group; a substituted or unsubstituted $C_6$ to $C_{40}$ aryl group; or a $C_2$ to $C_{40}$ heteroaryl group.

In another embodiment, $R_1$ and $R_2$ are the same as or different from each other, and may be each independently hydrogen; a halogen group; an ester group; a $C_1$ to $C_{40}$ alkyl group unsubstituted or substituted with a halogen group; a $C_6$ to $C_{40}$ aryl group unsubstituted or substituted with one or more substituents selected from the group consisting of a haloalkyl group, a halogen group and an alkyl ester group; or a $C_2$ to $C_{40}$ heteroaryl group.

In another embodiment, $R_1$ and $R_2$ are the same as or different from each other, and may be each independently hydrogen; a halogen group; an ester group; a $C_1$ to $C_{40}$ alkyl group unsubstituted or substituted with a halogen group; a $C_6$ to $C_{40}$ aryl group unsubstituted or substituted with a haloalkyl group, a halogen group and a methyl ester group; or a $C_2$ to $C_{40}$ heteroaryl group.

In another embodiment, $R_1$ and $R_2$ are the same as or different from each other, and may be each independently hydrogen; a $C_1$ to $C_{40}$ alkyl group; a $C_6$ to $C_{40}$ aryl group unsubstituted or substituted with a methyl ester group; or a substituted or unsubstituted $C_2$ to $C_{40}$ N-containing heteroaryl group.

In another embodiment, $R_1$ and $R_2$ are the same as or different from each other, and may be each independently hydrogen; a methyl group; a trifluoromethyl group; a pyridine group; a pyrimidine group; or a phenyl group unsubstituted or substituted with one or more substituents selected from the group consisting of a trifluoromethyl group, a halogen group and a methyl ester group.

In another embodiment, $R_1$ and $R_2$ may be any one selected from among the following structural formulae

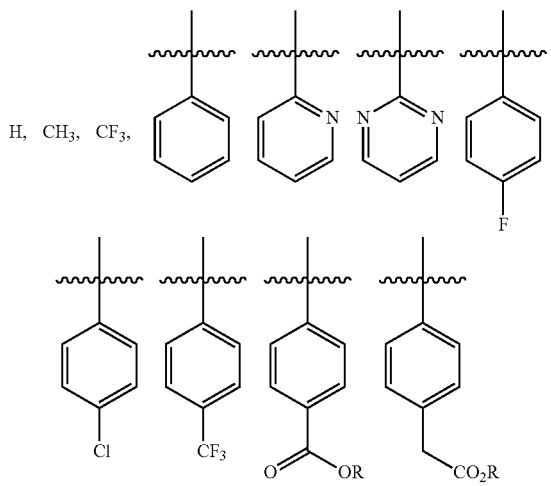

In the structural formulae,

R is hydrogen; a substituted or unsubstituted alkyl group; a substituted or unsubstituted aryl group; or a substituted or unsubstituted heteroaryl group.

In the structural formulae,

means a site linked to substituents.

By $R_1$ and $R_2$ having the above-mentioned substituents, high compatibility may be obtained depending on the type of a resin included in a photoresist composition afterward.

In one embodiment of the present application, $R_3$ may be a substituted or unsubstituted $C_1$ to $C_{60}$ alkyl group.

In another embodiment, $R_3$ may be a substituted or unsubstituted $C_1$ to $C_{30}$ alkyl group.

In another embodiment, $R_3$ may be a $C_1$ to $C_{30}$ alkyl group.

In another embodiment, $R_3$ may be a methyl group.

In one embodiment of the present application, $R_4$ to $R_6$ are the same as or different from each other, and may be each independently a substituted or unsubstituted $C_6$ to $C_{60}$ aryl group.

In another embodiment, $R_4$ to $R_6$ are the same as or different from each other, and may be each independently a substituted or unsubstituted $C_6$ to $C_{40}$ aryl group.

In another embodiment, $R_4$ to $R_6$ are the same as or different from each other, and may be each independently a $C_6$ to $C_{40}$ aryl group.

In another embodiment, $R_1$ to $R_6$ may be a phenyl group.

In one embodiment of the present application, $Ar_1$ and $Ar_2$ are the same as or different from each other, and may be each independently hydrogen; or a halogen group, and at least one of $Ar_1$ and $Ar_2$ may comprise a halogen group.

In another embodiment, $Ar_1$ and $Ar_2$ are the same as or different from each other, and may be each independently hydrogen; or a fluoro group, and at least one of $Ar_1$ and $Ar_2$ may comprise a fluoro group.

In the compound provided in one embodiment of the present application, the compound represented by Chemical Formula 1 is any one of the following compounds.

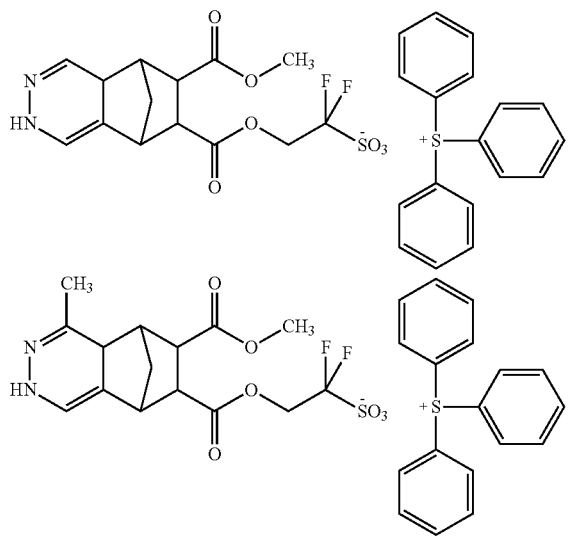

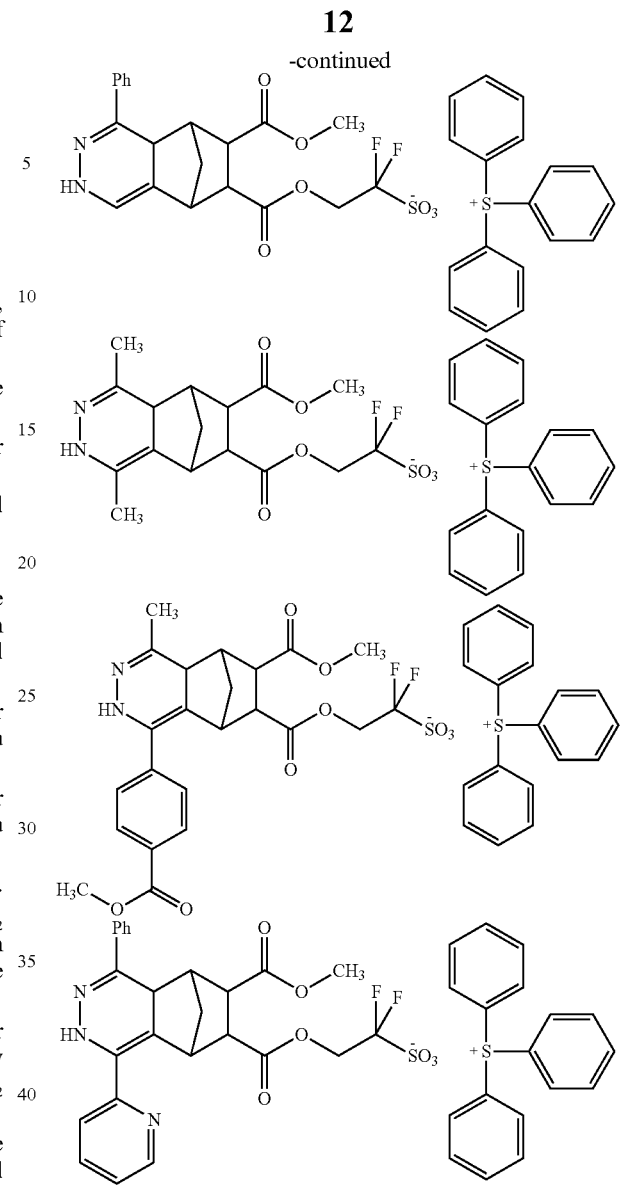

One embodiment of the present application provides a photoresist composition comprising a resin; the compound according to the present application; a photoacid generator (PAG); an acid diffusion control agent; and a quencher.

The photoresist composition comprising the compound according to the present application is capable of high resolution and freely forming pattern shapes by comprising the compound.

Particularly, the photoresist composition according to the present application comprises the compound of Chemical Formula 1 as a photo-degradable base, and is thereby capable of further enhancing contrast of an exposed portion and an unexposed portion, and is capable of improving line width roughness (LWR) without reducing sensitivity.

The photoresist composition is used for, for example, forming a micro or nanopattern used in a process for manufacturing a microelectronic device to manufacture small electronic components when manufacturing computer chips and integrated circuits, and such a pattern-forming process is referred to as a lithography process. A lithography process using a substrate material such as a silicon-based wafer used for manufacturing an integrated circuit is generally as follows.

A thin photoresist layer is formed on a substrate using a photoresist composition coating film or a photoresist film, and then the result is baked to fix the photoresist layer on the substrate. The photoresist layer fixed on the substrate is image-wise exposed to radiation. The exposed photoresist layer is treated with a developing solution, and by dissolving and removing the exposed area of the photoresist layer, a micro or nanopattern is formed.

In one embodiment of the present application, the resin may comprise one or more selected from the group consisting of a (meth)acrylate-based resin; a norbornene resin; a styrene-based resin; and an epoxy resin.

In one embodiment of the present application, the resin comprises one or more monomers selected from among monomers represented by the following Chemical Formulae 2 and 3.

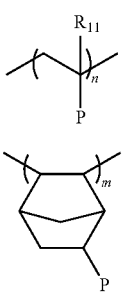

[Chemical Formula 2]

[Chemical Formula 3]

In Chemical Formulae 2 and 3, $R_{11}$ is hydrogen; a halogen group; a substituted or unsubstituted alkyl group; a substituted or unsubstituted aryl group; or a substituted or unsubstituted heteroaryl group, P is hydrogen; a halogen group; a nitrile group; a hydroxyl group; a substituted or unsubstituted ester group; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and m and n are each an integer of 1 to 100.

In one embodiment of the present application, the resin comprises one or more monomers selected from among monomers represented by the following Chemical Formulae 2-1 and 3-1.

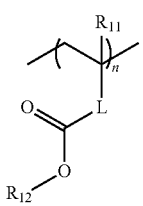

[Chemical Formula 2-1]

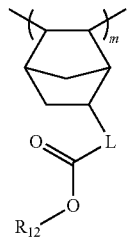

[Chemical Formula 3-1]

In Chemical Formulae 2-1 and 3-1,

L is a direct bond; a substituted or unsubstituted alkylene group; a substituted or unsubstituted arylene group; or a substituted or unsubstituted heteroarylene group, $R_{11}$ is hydrogen; a halogen group; a substituted or unsubstituted alkyl group; a substituted or unsubstituted aryl group; or a substituted or unsubstituted heteroaryl group, $R_{12}$ is hydrogen; a halogen group; a hydroxyl group; a substituted or unsubstituted alkyl group; a substituted or unsubstituted cycloalkyl group; a substituted or unsubstituted aryl group; or a substituted or unsubstituted heteroaryl group, and m and n are each an integer of 1 to 100.

In one embodiment of the present application, L may be a direct bond.

In one embodiment of the present application, $R_{11}$ may be hydrogen; or a substituted or unsubstituted alkyl group.

In another embodiment, $R_{11}$ may be a substituted or unsubstituted C1 to C60 alkyl group.

In another embodiment, $R_{11}$ may be a substituted or unsubstituted C1 to C40 alkyl group.

In another embodiment, $R_{11}$ may be a linear C1 to C40 alkyl group.

In another embodiment, $R_{11}$ may be a methyl group.

In one embodiment of the present application, $R_{12}$ may be any one selected from among the following structural formulae

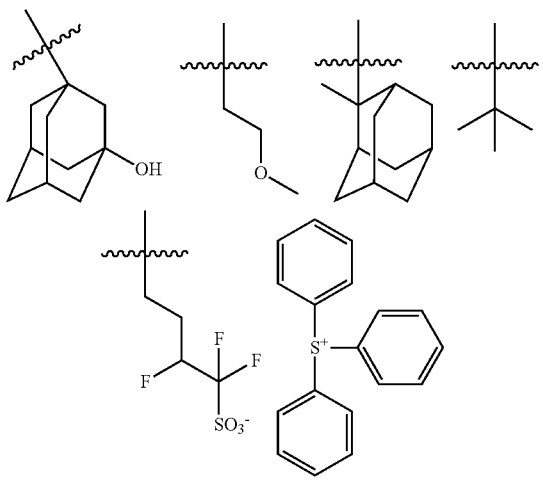

In the structural formulae,

means a site linked to O of Chemical Formula 2-1 or 3-1.

In one embodiment of the present application, the resin may have a weight average molecular weight of greater than or equal to 3000 g/mol and less than or equal to 15000 g/mol, and preferably greater than or equal to 3500 g/mol and less than or equal to 13000 g/mol.

By the weight average molecular weight of the resin satisfying the above-mentioned range, a photoresist pattern formed afterward has excellent sensitivity, and has no cracks formed thereon.

The weight average molecular weight is one of average molecular weights in which molecular weights are not uniform and a molecular weight of a certain polymer material is used as a base, and is a value obtained by averaging molecular weights of component molecular species of a polymer compound having molecular weight distribution by a weight fraction.

The weight average molecular weight may be measured through a gel permeation chromatography (GPC) analysis.

The resin is a polymer dissociated by an acid and thereby having increased solubility for an alkali developing solution, and due to a structure of the polymer main chain, a glass transition temperature is very high suppressing acid diffusion, and as a result, high resolution is obtained.

In one embodiment of the present application, the photoacid generator is a material generating an acid by receiving light, and is a material increasing solubility by having an unstable group of a resin to react, and enabling patterning of a photoresist pattern comprising the same afterward.

The photoacid generator is preferably a salt of a cation and an anion. The photoacid generator preferably has sufficiently low radiation absorption at the wavelength of exposure, and does not directly generate an acid with respect to radiation at the time of exposure. As a result, in the photoresist composition, an acid may be generated by a photosensitive reaction only in an exposed portion of a pattern during exposure.

The photoacid generator may specifically comprise an onium salt compound, a diazomethane compound, a sulfonimide compound and the like. Examples of the onium salt compound may comprise a sulfonium salt compound, a tetrahydrothiophenium salt compound, an iodonium salt compound and the like. The photoacid generator preferably comprises at least one type selected from the group consisting of an sulfonium salt compound, an iodonium salt compound, sulfonyl diazomethane, N-sulfonyl oxyimide and oxime-O-sulfonate type photoacid generators, and more preferably comprises at least one type of compound selected from the group consisting of a sulfonium salt compound and an iodonium salt compound.

In one embodiment of the present application, specific examples of the sulfonium salt compound may comprise triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate and the like.

Specific examples of the iodonium salt compound may comprise diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate and the like.

In one embodiment of the present application, the photoacid generator may be represented by the following Chemical Formula 4.

[Chemical Formula 4]

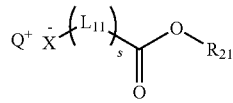

In Chemical Formula 4, $L_{11}$ is a direct bond; a substituted or unsubstituted alkylene group; a substituted or unsubstituted arylene group; or a substituted or unsubstituted heteroarylene group, s is an integer of 1 to 5, and when s is 2 or greater, $L_{11}$s are the same as or different from each other, $Q^+$ is an onium cation, $X^-$ is an acid anion, and $R_{21}$ is hydrogen; a substituted or unsubstituted alkyl group; a substituted or unsubstituted cycloalkyl group; a substituted or unsubstituted aryl group; or a substituted or unsubstituted heteroaryl group.

In one embodiment of the present application, $X^-$ is an acid anion, and the acid anion may be one type of anion group selected from the group consisting of a sulfonic acid anion, a carboxylic acid anion, a sulfonylimide anion, a bis(alkylsulfonyl)imide anion and a tris(alkylsulfonyl)methide anion.

In one embodiment of the present application, $X^-$ may be $-SO_3^-$.

In one embodiment of the present application, $Q^+$ may be an onium cation.

The onium cation may be an onium cation comprising an S; I; O; N; P; Cl; Br; F; As; Se; Sn; Sb; Te; or Bi element.

In another embodiment, $Q^+$ may be represented by the following Chemical Formula 4-1.

[Chemical Formula 4-1]

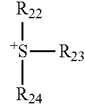

In Chemical Formula 4-1, $R_{22}$ to $R_{24}$ are a substituted or unsubstituted aryl group; or a substituted or unsubstituted heteroaryl group.

In one embodiment of the present application, $L_{11}$ may be a direct bond; a substituted or unsubstituted alkylene group; a substituted or unsubstituted arylene group; or a substituted or unsubstituted heteroarylene group.

In another embodiment, $L_{11}$ may be a direct bond; a substituted or unsubstituted C1 to C60 alkylene group; a substituted or unsubstituted C6 to C60 arylene group; or a substituted or unsubstituted C2 to C60 heteroarylene group.

In another embodiment, $L_{11}$ may be a direct bond; or a substituted or unsubstituted C1 to C60 alkylene group.

In another embodiment, $L_{11}$ may be a direct bond; or a C1 to C60 alkylene group unsubstituted or substituted with a halogen group.

In another embodiment, $L_{11}$ may be a direct bond; or a C1 to C40 alkylene group unsubstituted or substituted with a halogen group.

In another embodiment, $L_{11}$ may be a direct bond; or a C1 to C40 alkylene group unsubstituted or substituted with a fluoro group (—F).

In another embodiment, $L_{11}$ may be a direct bond; or a methylene group unsubstituted or substituted with a fluoro group (—F).

In one embodiment of the present application, $R_{22}$ to $R_{24}$ may be a substituted or unsubstituted C6 to C60 aryl group.

In another embodiment, $R_{22}$ to $R_{24}$ may be a C6 to C60 aryl group unsubstituted or substituted with a C1 to C60 alkyl group.

In another embodiment, $R_{22}$ to $R_{24}$ may be a C6 to C40 aryl group unsubstituted or substituted with a C1 to C40 alkyl group.

In another embodiment, $R_{22}$ to $R_{24}$ may be a phenyl group unsubstituted or substituted with a tert-butyl group.

In one embodiment of the present application, $R_{21}$ may be a substituted or unsubstituted alkyl group; or a substituted or unsubstituted cycloalkyl group.

In another embodiment, $R_{21}$ may be a substituted or unsubstituted C1 to C60 alkyl group; or a substituted or unsubstituted C3 to C60 cycloalkyl group.

In one embodiment of the present application, the photoacid generator may be represented by the following structure.

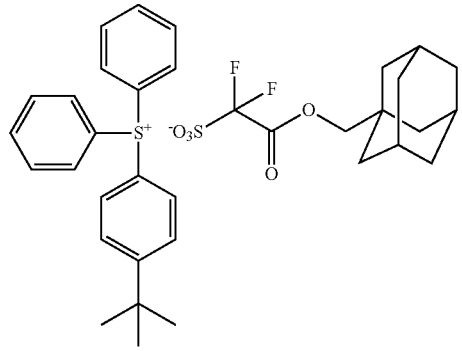

In one embodiment of the present application, the acid diffusion control agent and the quencher are materials suppressing a reaction in an unexposed portion caused by an acid generated in the exposed portion diffusing to the unexposed portion.

In one embodiment of the present application, the acid diffusion control agent and the quencher may be represented by the following Chemical Formula 5.

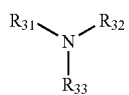

[Chemical Formula 5]

In Chemical Formula 5, $R_{31}$ to $R_{33}$ are selected from the group consisting of a substituted or unsubstituted alkyl group; and a substituted or unsubstituted an ester group, or adjacent two or more groups bond to form a substituted or unsubstituted aliphatic hydrocarbon ring or a substituted or unsubstituted heteroring.

In one embodiment of the present application, the acid diffusion control agent and the quencher may be any one selected from among the following structural formulae.

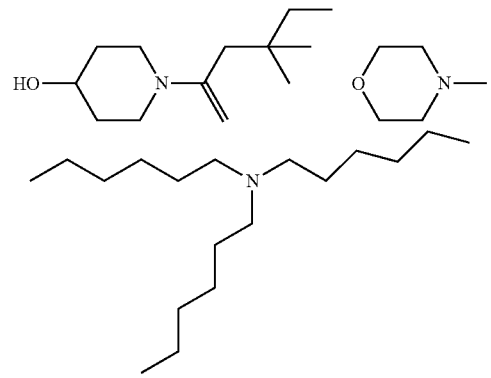

In one embodiment of the present application, the photoresist composition may further comprise a solvent, and the solvent may be one or more types selected from the group consisting of acetone, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxypropanol, 2-methoxypropanol, 3-methoxybutanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, propylene glycol monomethyl ether and dipropylene glycol monomethyl ether, but is not limited thereto.

As the solvent, propylene glycol methyl ether acetate (PGMEA) may be preferably used.

In one embodiment of the present application, the photoresist composition may further comprise one or more selected from the group consisting of a surfactant; a photosensitizer; and a photobase generator.

In one embodiment of the present application, the surfactant may be used without limit as long as it is a material performing a role of suppressing bubble generation in the photoresist composition, enhancing adhesive strength, and increasing coating uniformity.

In one embodiment of the present application, the photosensitizer is a material increasing activity of the photoacid generator, and is a material performing a role of increasing photoresist pattern sensitivity.

In one embodiment of the present application, the photobase generator may be used without limit as long as it is a material generating a base by receiving light.

In the photoresist composition provided in one embodiment of the present application, the photoresist composition comprises the compound in greater than or equal to 0.1 parts by weight and less than or equal to 20 parts by weight based on 100 parts by weight of the resin.

In another embodiment, the photoresist composition may comprise the compound in greater than or equal to 0.1 parts by weight and less than or equal to 20 parts by weight, preferably in greater than or equal to 0.1 parts by weight and less than or equal to 15 parts by weight, and more preferably in greater than or equal to 0.2 parts by weight and less than or equal to 10 parts by weight based on 100 parts by weight of the resin.

In the photoresist composition provided in one embodiment of the present application, the photoresist composition comprises the photoacid generator in greater than or equal to 0.1 parts by weight and less than or equal to 20 parts by weight based on 100 parts by weight of the resin.

In another embodiment, the photoresist composition may comprise the photoacid generator in greater than or equal to 0.1 parts by weight and less than or equal to 20 parts by weight, preferably in greater than or equal to 1 parts by weight and less than or equal to 15 parts by weight, and more preferably in greater than or equal to 2 parts by weight and less than or equal to 10 parts by weight based on 100 parts by weight of the resin.

In the photoresist composition provided in one embodiment of the present application, the photoresist composition comprises the acid diffusion control agent in greater than or equal to 0.1 parts by weight and less than or equal to 20 parts by weight based on 100 parts by weight of the resin.

In another embodiment, the photoresist composition may comprise the acid diffusion control agent in greater than or equal to 0.1 parts by weight and less than or equal to 20 parts by weight, preferably in greater than or equal to 0.3 parts by weight and less than or equal to 10 parts by weight, and more preferably in greater than or equal to 0.5 parts by weight and less than or equal to 5 parts by weight based on 100 parts by weight of the resin.

In one embodiment of the present application, the photoresist composition may comprise the surfactant in greater than or equal to 0.01 parts by weight and less than or equal to 5 parts by weight based on 100 parts by weight of the resin.

In one embodiment of the present application, the photoresist composition may comprise the photosensitizer in greater than or equal to 0.1 parts by weight and less than or equal to 10 parts by weight based on 100 parts by weight of the resin.

In one embodiment of the present application, the photoresist composition may comprise the photobase generator in greater than or equal to 0.1 parts by weight and less than or equal to 10 parts by weight based on 100 parts by weight of the resin.

In the photoresist composition provided in one embodiment of the present application, the photoresist composition comprises the quencher in greater than or equal to 0.1 parts by weight and less than or equal to 10 parts by weight based on 100 parts by weight of the resin.

In another embodiment, the photoresist composition may comprise the quencher in greater than or equal to 0.1 parts by weight and less than or equal to 10 parts by weight, preferably in greater than or equal to 0.1 parts by weight and less than or equal to 5 parts by weight, and more preferably in greater than or equal to 0.2 parts by weight and less than or equal to 1 parts by weight based on 100 parts by weight of the resin.

By comprising the materials in the above-mentioned weight ranges, the photoresist composition is capable of obtaining high resolution and freely forming pattern shapes.

One embodiment of the present specification provides a photoresist pattern comprising the photoresist composition according to one embodiment of the present application.

In one embodiment of the present application, the photoresist composition may be included in the photoresist pattern as it is.

One embodiment of the present application provides a photoresist pattern formed using the photoresist composition.

In one embodiment of the present application, the photoresist pattern may be formed using the following preparation method.

In one embodiment of the present specification, a photolithography process forming a photoresist pattern using the photoresist composition may comprise forming a photoresist layer on a semiconductor substrate using the photoresist composition; selectively exposing the photoresist layer; and developing the exposed photoresist layer.

One embodiment of the present application provides a method for preparing a photoresist pattern, the method comprising forming a photoresist layer by coating a photoresist composition on a semiconductor substrate; selectively exposing the photoresist layer; and developing the exposed photoresist layer.

In one embodiment of the present application, the forming of a photoresist layer comprises coating a photoresist composition on a substrate; and drying (soft baking) the coated material.

In one embodiment of the present specification, as the method of coating the photoresist composition, a method of coating with a spin coater, a bar coater, a blade coater, a curtain coater, a screen printer or the like, a method of spraying with a spray coater, or the like, may be used, however methods capable of coating a photoresist composition may be used without limit.

In the drying (soft baking) of the coated material, the coated material may be dried under a condition of 30 seconds to 120 seconds at 70° C. to 180° C. The drying method may comprise, for example, an oven, a hot plate, vacuum drying and the like, but is not limited thereto. When going through the drying, a solvent is removed from the photoresist composition increasing adhesive strength between the wafer and the photosensitive resin layer, and the photoresist layer may be formed on the semiconductor substrate.

In one embodiment of the present application, the selectively exposing of the photoresist layer is aligning a mask on the photoresist, and exposing an area of the photoresist layer not covered by the mask to ultraviolet rays. The mask may be in contact with the photoresist layer, or may also be aligned at a certain distance from the photoresist layer.

In the exposure process, a light source irradiated as a light irradiation means may comprise electromagnetic waves, extreme ultraviolet rays (EUV), from ultraviolet rays to visible rays, an electron beam, X-rays, laser rays and the like. In addition, as a method of irradiating the light source, known means such as a high pressure mercury lamp, a xenon lamp, a carbon arc lamp, a halogen lamp, a cold cathode tube for a copier, an LED and a semiconductor laser may be used.

In one embodiment of the present application, the selectively exposing of the photoresist layer may further comprise heating (post-exposure baking) the exposed photoresist layer after the exposure. By heating the exposed photoresist layer, components in the photoresist composition are realigned, reducing a standing wave of the photoresist layer.

The heating (post-exposure baking) of the photoresist layer may be conducted under a condition of 30 seconds to 120 seconds at 70° C. to 180° C.

In one embodiment of the present application, the developing of the exposed photoresist layer is removing the exposed portion in the photoresist layer by immersing in a developing solution. As the developing method, photoresist developing methods known in the art such as a rotary spray method, a paddle method or an immersion method accompanying ultrasonic treatment may be used, however, the method is not limited thereto.

Examples of the developing solution may comprise alkali metal or alkaline earth metal hydroxides, carbonates, hydrogen carbonates, an aqueous basic solution such as an ammonia water quaternary ammonium salt may be used. Among these, an aqueous ammonia quaternary ammonium solution such as an aqueous tetramethyl ammonium solution is particularly preferred.

Through steps as above, the photoresist pattern according to one embodiment of the present application may be formed.

In one embodiment of the present disclosure, the method for forming a pattern of a photoresist layer may be used in a semiconductor manufacturing process.

Specifically, in one embodiment of the semiconductor manufacturing process, a process of etching an area of the semiconductor substrate not covered by the photoresist layer, and removing (ashing) the photoresist layer from the semiconductor substrate is further included in the photolithography process.

The etching of an area of the semiconductor substrate not covered by the photoresist layer is etching the semiconductor substrate area other than the pattern of the photoresist layer.

The removing of the photoresist layer from the semiconductor substrate may use known methods, and for example, may be conducted by heating a wafer in a low pressure state using a reaction chamber, and then injecting a plasma comprising an oxygen group or an oxygen ion thereto.

The semiconductor substrate is not limited, and those known in the art may be used. For example, substrates for electronic components, or those having a predetermined wiring pattern formed to thereon may be included as an example. Examples of the substrate for an electronic component may comprise substrates made of metal or glass substrates such as silicon, silicon nitride, titanium, tantalum, palladium, titanium tungsten, copper, chromium, iron, aluminum, gold and nickel, or the like. Examples of the wiring pattern material may comprise copper, solder, chromium, aluminum, nickel, gold and the like, but are not limited thereto.

One embodiment of the present specification provides an electronic device comprising the photoresist pattern.

The electronic device may be used without limit as long as it is capable of using a photoresist layer prepared from the composition according to the present specification. For example, it may be used in a wide range of applications such as circuit substrate manufacturing, electronic component manufacturing, connection terminals such as bumps or metal posts, and wiring patterns.

Hereinafter, the present specification will be described in detail with reference to examples in order to specifically describe the present specification. However, the examples according to the present specification may be modified to various other forms, and the scope of the present specification is not to be construed as being limited to the examples described below. Examples of the present specification are provided in order to more fully describe the present specification to those having average knowledge in the art.

PREPARATION EXAMPLE

Synthesis of Compounds

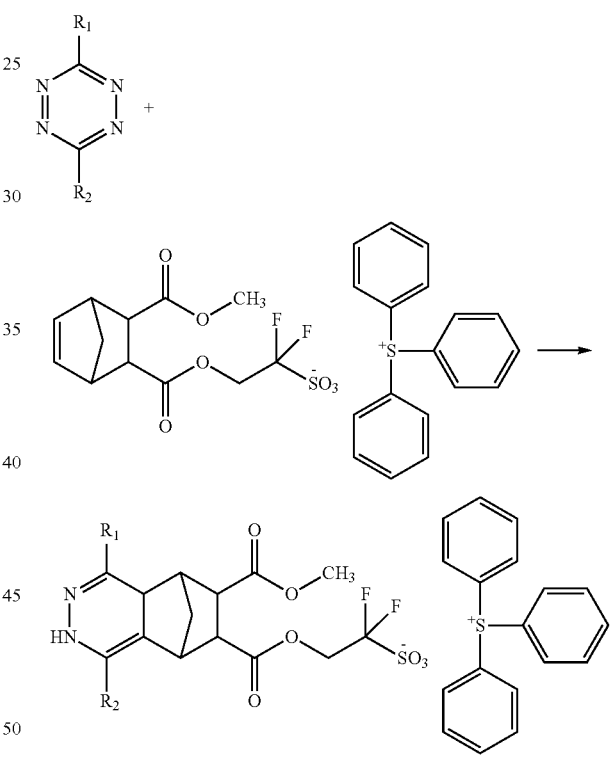

In the syntheses of the compounds, the compounds were synthesized using substituents described in the following Table 1.

TABLE 1

|  | $R_1$ | $R_2$ | Yield (%) |
|---|---|---|---|
| Preparation Example 1 | H | H | 95 |
| Preparation Example 2 | $CH_3$ | H | 93 |
| Preparation Example 3 | Ph | H | 94 |
| Preparation Example 4 | $CH_3$ | $CH_3$ | 93 |
| Preparation Example 5 | $CH_3$ | $4\text{-}CO_2CH_3P\text{—}C_6H_4$ | 90 |
| Preparation Example 6 | Ph | 2-Pyridinyl | 91 |

Preparation of Intermediate 1

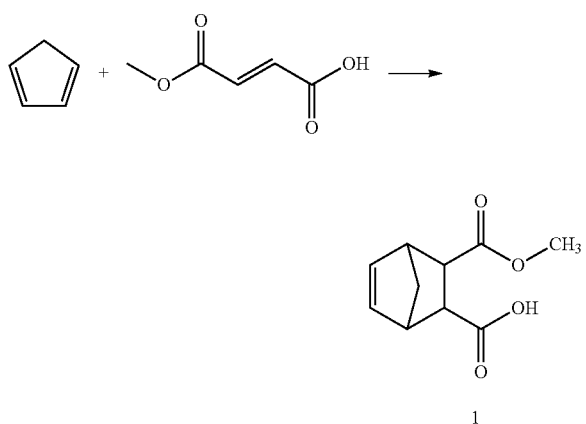

Cyclopentadiene (132.2 g, 2.0 mol), 2-carboxyethyl acrylate (130.1 g, 1.0 mol) and 4-methoxyphenol (2.4 g, 0.02 mol) were introduced to a high pressure reactor, and the result was reacted for 18 hours at 180° C., and then vacuum distilled to obtain Intermediate 1 (190 g, 97%).

1H-NMR (CDCl3): (ppm) δ=6.3 (dd, H), 6.2 (dd, H), 3.6 (s, 3H), 3.34 (dd, H), 3.29 (dd, H), 3.2-3.1 (m, 2H), 1.5 (m, H), 1.4-1.3 (br, H)

Preparation of Intermediate 2

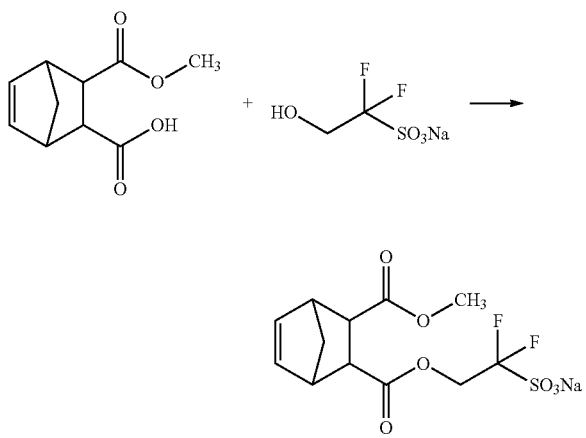

Intermediate 1 (196 g, 1.0 mol), sodium 1,1-difluoro-2-hydroxyethane-1-sulfonate (220.9 g, 1.2 mol) and $H_2SO_4$ (19.6 g, 0.2 mol) were introduced and reacted for 6 hours at 60° C. After the reaction was finished, $H_2O$ (1 L) was introduced thereto, the result was extracted 3 times with ethyl acetate (1 L), and the solvent was removed. The obtained result was recrystallized with EtOH to obtain Intermediate 2 (330 g, 91%).

1H-NMR (DMSO-D6): (ppm) δ=6.1-6.0 (m, 2H), 4.9 (m, 2H), 3.7-3.5 (m, 5H), 3.1-2.9 (m, 2H), 1.8-1.5 (m, 2H)

Preparation of Intermediate 3

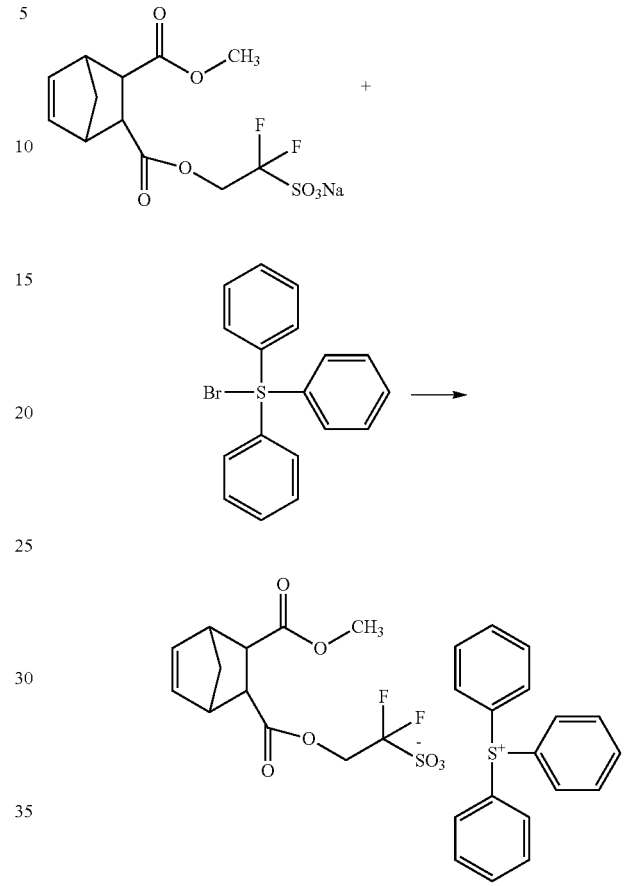

Intermediate 2 (181 g, 0.5 mol) and triphenylsulfonium bromide (172 g, 0.5 mol) were introduced to a $H_2O$:dichloro-methane=1:1 solution (1 L), and reacted for 12 hours at room temperature (25° C.). After the reaction was finished, the organic layer was washed 3 times with $H_2O$ (1 L), and then diethyl ether was introduced thereto to form precipitates. The precipitates were filtered and then dried to obtain Intermediate 3 (compound B1) (280 g, 93%).

1H-NMR (DMSO-D6): (ppm) δ=7.4-7.1 (m, 15H), 6.1-6.0 (m, 2H), 4.5 (m, 2H), 3.7-3.5 (m, 5H), 3.1-2.9 (m, 2H), 1.8-1.5 (m, 2H)

Preparation of Intermediate 4

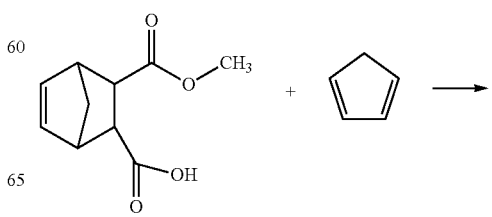

-continued

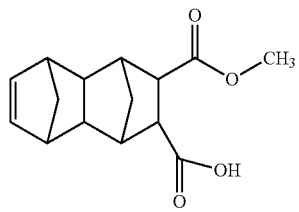

Intermediate 1 (196.0 g, 1.0 mol), cyclopentadiene (132.2 g, 2.0 mol) and 4-methoxyphenol (2.4 g, 0.02 mol) were introduced to a high pressure reactor, reacted for 18 hours at 180° C., and then vacuum distilled to obtain Intermediate 4 (250 g, 95%).

1H-NMR (DMSO-D6): (ppm) δ=6.1-6.0 (m, 2H), 3.6 (s, 3H), 2.8 (m, H), 2.6-2.4 (m, 3H), 2.2-1.6 (m, 4H), 1.2 (m, 2H), 1.0-0.7 (m, 2H)

Preparation of Intermediate 5

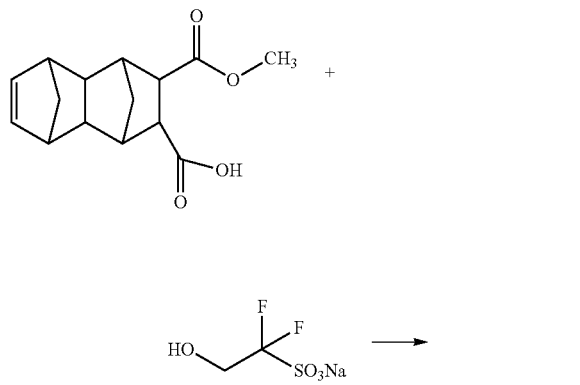

Intermediate 4 (131.0 g, 0.5 mol), sodium 1,1-difluoro-2-hydroxyethane-1-sulfonate (110.5 g, 0.6 mol) and $H_2SO_4$ (9.8 g, 0.1 mol) were introduced and reacted for 6 hours at 60° C. After the reaction was finished, $H_2O$ (1 L) was introduced thereto, the result was extracted 3 times with ethyl acetate (1 L), and the solvent was removed. The obtained result was recrystallized with EtOH to obtain Intermediate 5 (196.9 g, 92%).

1H-NMR (DMSO-D6): (ppm) δ=6.1-6.0 (m, 2H), 4.9 (dd, 2H), 3.7 (s, 3H), 2.85 (m, H), 2.6-2.4 (m, 3H), 2.2-1.6 (m, 4H), 1.2 (m, 2H), 1.1-0.7 (m, 2H)

Preparation of Intermediate 6

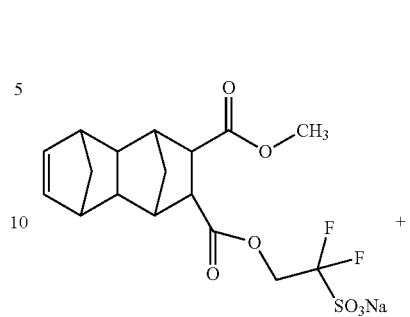

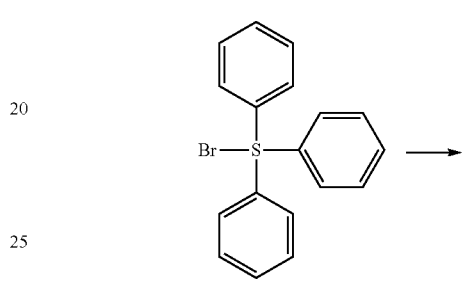

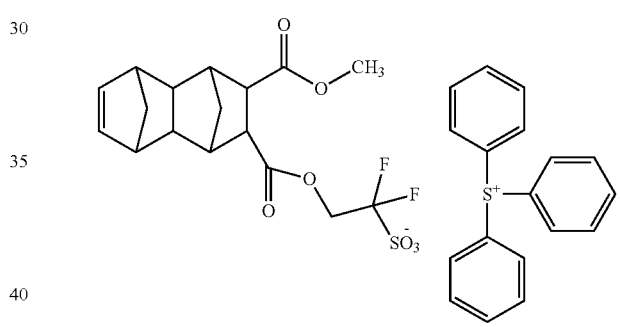

Intermediate 5 (214.0 g, 0.5 mol) and triphenylsulfonium bromide (172 g, 0.5 mol) were introduced to a $H_2O$:dichloro-methane=1:1 solution (1 L), and reacted for 12 hours at room temperature (25° C.). After the reaction was finished, the organic layer was washed 3 times with $H_2O$ (1 L), and then diethyl ether was introduced thereto to form precipitates. The precipitates were filtered and then dried to obtain Intermediate 6 (compound B2) (314.0 g, 94%).

1H-NMR (DMSO-D6): (ppm) δ=7.4-7.1 (m, 15H), 6.2-6.0 (m, 2H), 4.9 (dd, 2H), 3.7 (s, 3H), 2.85 (m, H), 2.6-2.4 (m, 3H), 2.2-1.6 (m, 4H), 1.2 (m, 2H), 1.1-0.7 (m, 2H)

Specific syntheses of Preparation Example 1 to Preparation Example 6 described in Table 1 are as follows.

Preparation Example 1

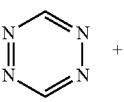

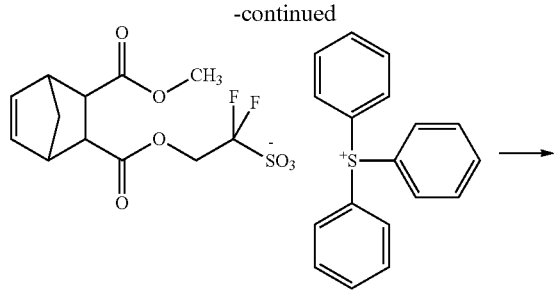

1,2,4,5-Tetrazine (4.5 g, 0.055 mol) and Intermediate 3 (30 g, 0.05 mol) were introduced to dichloromethane (1 L), and the result was reacted for 12 hours at room temperature. After the reaction was finished, diethyl ether was introduced thereto to form precipitates, and the precipitates were filtered and then dried to obtain A1 (31.2 g, 95%).

1H-NMR (DMSO-D6): (ppm) δ=7.5 (d, H), 7.4-7.1 (m, 15H), 5.7 (s, H), 4.5 (m, 2H), 3.7 (s, 3H), 3.1-2.8 (m, 3H), 2.3-2.2 (m, H), 2.1-2.0 (m, H), 1.7-1.4 (m, 2H)

Preparation Example 2

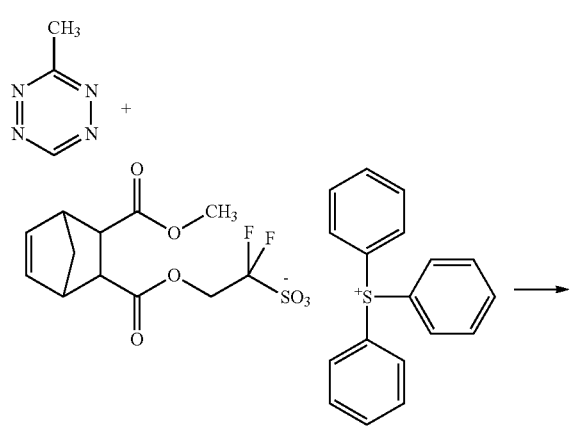

3-Methyl-1,2,4,5-tetrazine (5.2 g, 0.055 mol) and Intermediate 3 (30 g, 0.05 mol) were introduced to dichloromethane (1 L), and the result was reacted for 12 hours at room temperature (25° C.). After the reaction was finished, diethyl ether was introduced thereto to form precipitates, and the precipitates were filtered and then dried to obtain A2 (31.2 g, 93%).

1H-NMR (DMSO-D6): (ppm) δ=7.4-7.1 (m, 15H), 5.6 (s, H), 4.4 (m, 2H), 3.7 (s, 3H), 3.1-2.8 (m, 3H), 2.4-1.9 (m, 5H), 1.7-1.4 (m, 2H)

Preparation Example 3

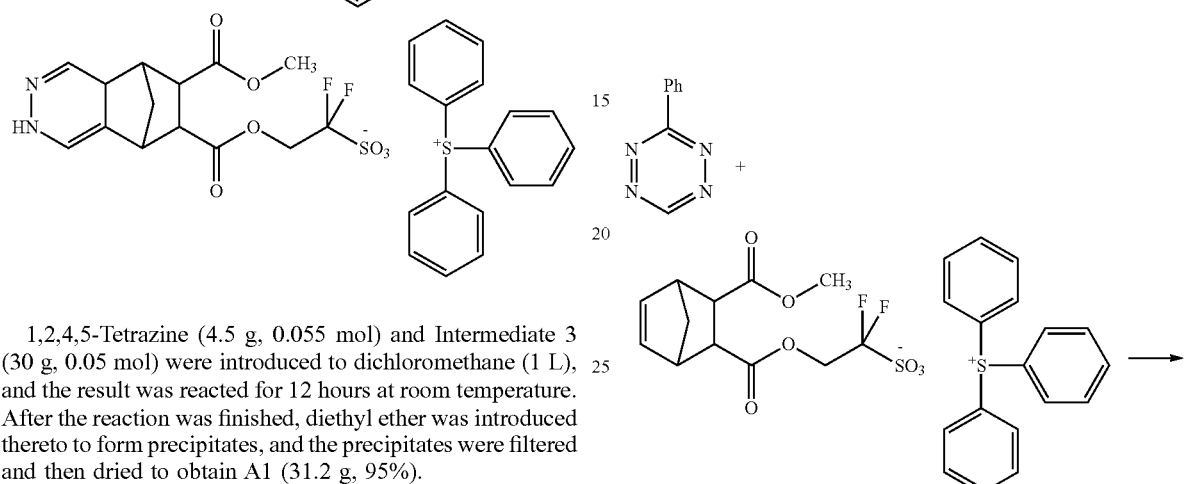

3-Phenyl-1,2,4,5-tetrazine (8.7 g, 0.055 mol) and Intermediate 3 (30 g, 0.05 mol) were introduced to dichloromethane (1 L), and the result was reacted for 12 hours at room temperature (25° C.). After the reaction was finished, diethyl ether was introduced thereto to form precipitates, and the precipitates were filtered and then dried to obtain A3 (34.4 g, 94%).

1H-NMR (DMSO-D6): (ppm) δ=7.9 (m, 2H), 7.5-7.1 (m, 18H), 5.6 (s, H), 4.4 (m, 2H), 3.7 (s, 3H), 3.1-2.8 (m, 3H), 2.2-1.9 (m, 2H), 1.7-1.4 (m, 2H)

Preparation Example 4

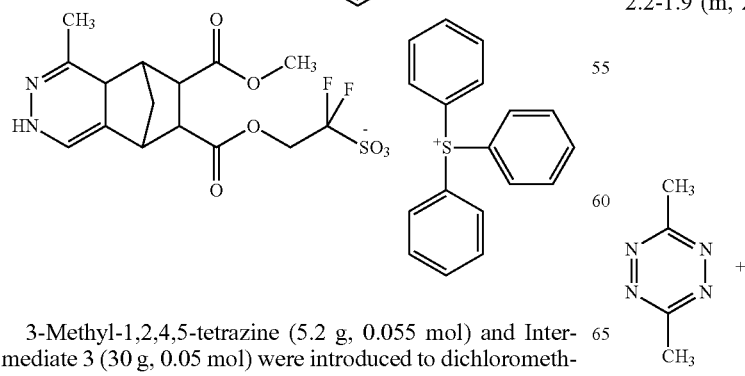

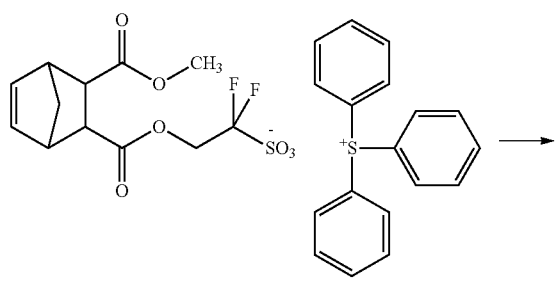

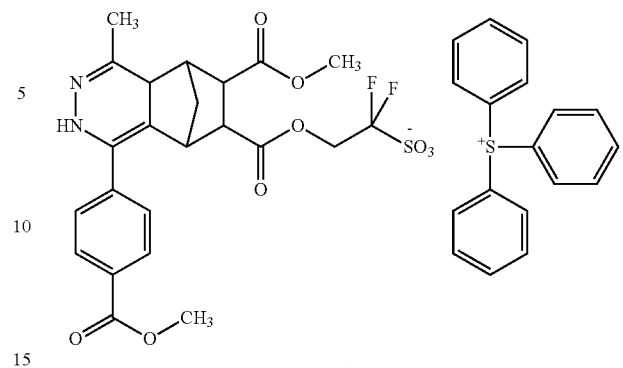

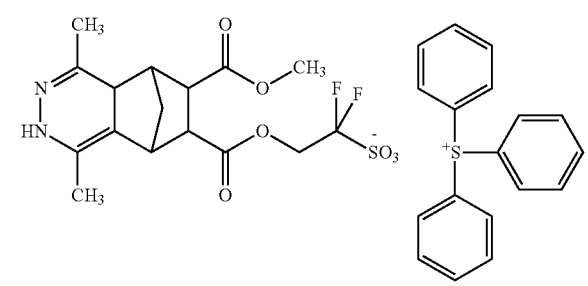

3,6-Dimethyl-1,2,4,5-tetrazine (6.1 g, 0.055 mol) and Intermediate 3 (30 g, 0.05 mol) were introduced to dichloromethane (1 L), and the result was reacted for 12 hours at room temperature (25° C.). After the reaction was finished, diethyl ether was introduced thereto to form precipitates, and the precipitates were filtered and then dried to obtain A4 (31.8 g, 94%).

1H-NMR (DMSO-D6): (ppm) δ=7.4-7.1 (m, 15H), 4.4 (m, 2H), 3.7 (s, 3H), 3.2-2.8 (m, 3H), 2.5-1.9 (m, 8H), 1.7-1.4 (m, 2H)

Preparation Example 5

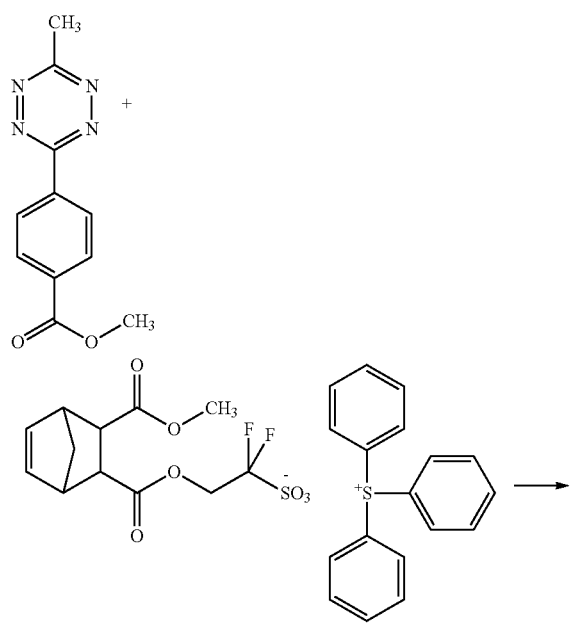

Methyl 4-(6-methyl-1,2,4,5-tetrazin-3-yl)benzoate (12.7 g, 0.055 mol) and Intermediate 3 (30 g, 0.05 mol) were introduced to dichloromethane (1 L), and the result was reacted for 12 hours at mom temperature (25° C.). After the reaction was finished, diethyl ether was introduced thereto to form precipitates, and the precipitates were filtered and then dried to obtain A5 (36.2 g, 90%).

1H-NMR (DMSO-D6): (ppm) δ=7.4-7.1 (m, 19H), 4.4 (m, 2H), 3.9 (s, 3H), 3.7 (s, 3H), 3.2-2.8 (m, 3H), 2.5-1.9 (m, 5H), 1.7-1.4 (m, 2H)

Preparation Example 6

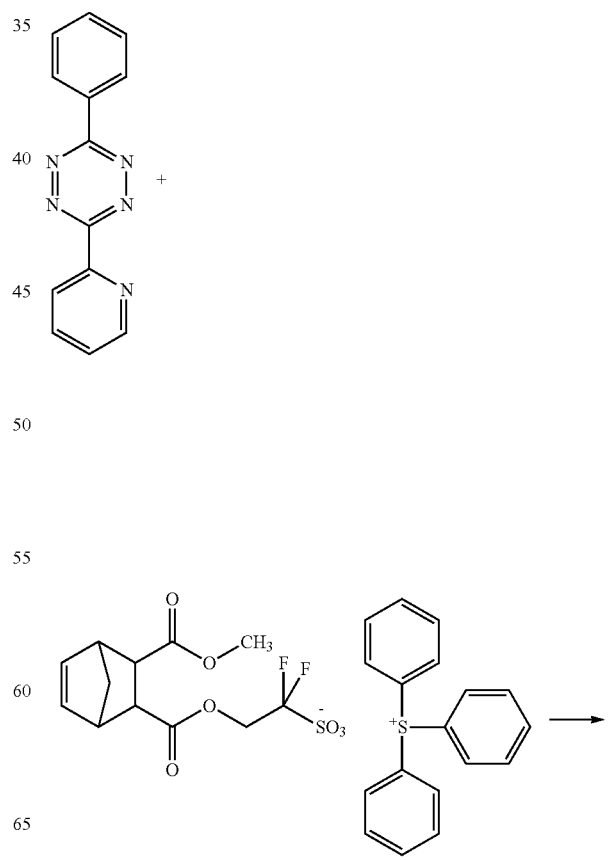

-continued

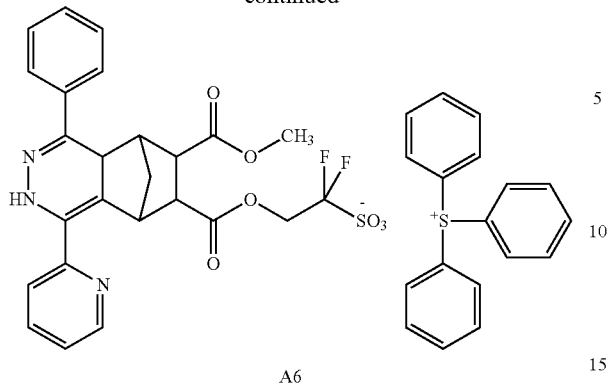

A6

3-Phenyl-6-(pyridin-2-yl)-1,2,4,5-tetrazine (12.9 g, 0.055 mol) and Intermediate 3 (30 g, 0.05 mol) were introduced to dichloro-methane (1 L), and the result was reacted for 12 hours at room temperature (25° C.). After the reaction was finished, diethyl ether was introduced thereto to form precipitates, and the precipitates were filtered and then dried to obtain A6 (36.9 g, 91%).

1H-NMR (DMSO-D6): (ppm) δ=8.5 (d, H), 7.9 (m, 2H), 7.4-7.1 (m, 21H), 4.4 (m, 2H), 3.7 (s, 3H), 3.1-2.8 (m, 3H), 2.2-1.9 (m, 2H), 1.7-1.4 (m, 2H)

Synthesis of Resin

Polymer R1

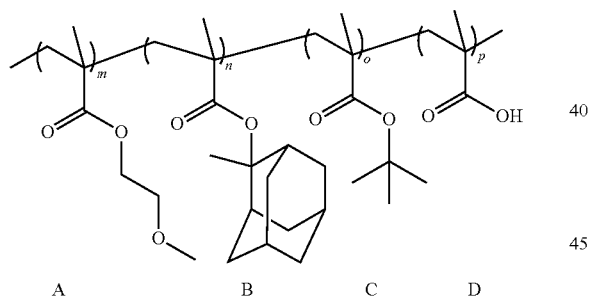

Composition A:B:C:D=50:20:20:10 Mw 6,000

2-methoxyethyl methacrylate (72 g, 0.5 mol), 2-methyl-2-adamantyl methacrylate (46.8 g, 0.2 mol), tert-butyl methacrylate (28.4 g, 0.2 mol), methacrylic acid (8.6 g, 0.1 mol) and tetrahydrofuran (THF) (150 g) were introduced to a flask, and stirred for 20 minutes under the nitrogen atmosphere.

AIBN (11.5 g, 0.07 mol) was dissolved in THF (10 g) to prepare an initiator solution. After heating the reaction solution to 65° C., the initiator solution was introduced thereto, and the result was stirred for 18 hours. After the reaction was finished, the reaction solution was diluted with acetone, and precipitates were formed using an excess amount of hexane. The precipitates were filtered, and then dried for 18 hours in a 30° C. oven to collect a polymer. A weight average molecular weight of Polymer R1 measured using gel permeation chromatography (GPC) was 6,000 g/mol.

Polymer R2

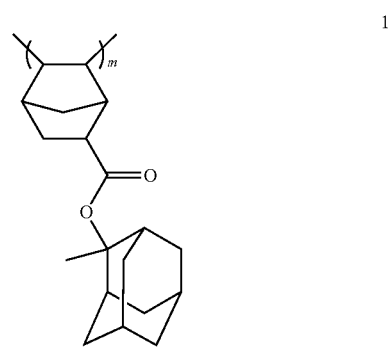

Norbornene Monomer 1 (17.1 g, 0.06 mol), Norbornene Monomer 2 (11.5 g, 0.04 mol) and anisole (28.6 g) was introduced to a flask, and stirred for 20 minutes under the nitrogen atmosphere. A palladium catalyst was dissolved in anisole (1 g) under the argon atmosphere to prepare a palladium catalyst solution. After heating the reaction solution to 80° C., the palladium catalyst solution was introduced thereto, and the result was stirred for 18 hours. After the reaction was finished, the reaction solution was diluted with THF, and precipitates were formed using an excess amount of hexane. The precipitates were filtered, and then dried for 18 hours in a 30° C. oven to collect a polymer. A weight average molecular weight of Polymer R2 measured using gel permeation chromatography (GPC) was 5,000 g/mol.

Polymer R3

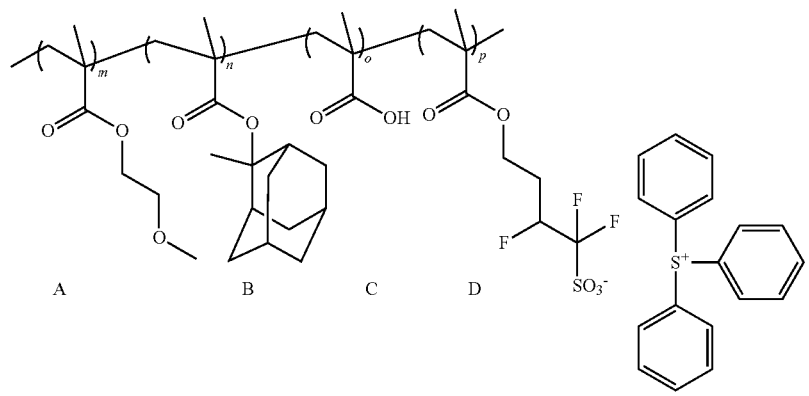

Composition A:B:C:D=50:20:20:10 Mw 6,500

Polymerization was conducted in the same manner as with Polymer R1. A weight average molecular weight of Polymer R3 measured using gel permeation chromatography (GPC) was 6,500 g/mol.

Polymer R4

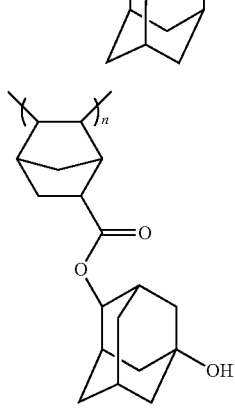

-continued

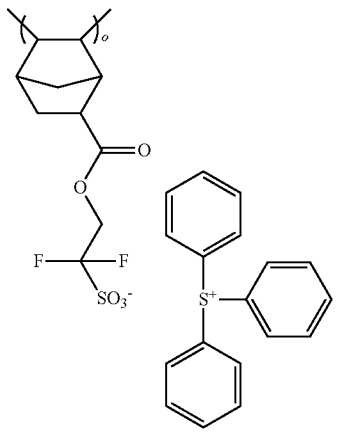

Composition A:B:C=60:30:10 Mw 5,500

Polymerization was conducted in the same manner as with Polymer R2. A weight average molecular weight of Polymer R4 measured using gel permeation chromatography (GPC) was 5,500 g/mol.

With each of the compounds and the polymers according to Preparation Examples 1 to 6, a photoresist composition comprising a content and a material of the following Table 2 was prepared.

TABLE 2

| | Resin | | Photoacid Generator (Mass %) | Quencher (Mass %) | Compound (Mass %) | Dose mJ/cm$^2$ | Evaluation | LWR nm | Evaluation |
|---|---|---|---|---|---|---|---|---|---|
| Example 1 | R1 (60%) | R3 (40%) | 5.0 | 0.5 | A1 0.5 | 75 | Δ | 7.7 | ○ |
| Example 2 | R1 (60%) | R3 (40%) | 5.0 | 0.5 | A3 0.5 | 64 | ○ | 8.3 | ○ |

TABLE 2-continued

|  | Resin | Photoacid Generator (Mass %) | Quencher (Mass %) | Compound (Mass %) | Dose mJ/cm$^2$ | Evaluation | LWR nm | Evaluation |
|---|---|---|---|---|---|---|---|---|
| Example 3 | R1 (60%) R4 (40%) | 5.0 | 0.5 | A2 0.5 | 58 | ○ | 8.4 | ○ |
| Example 4 | R1 (60%) R4 (40%) | 5.0 | 0.5 | A4 0.5 | 52 | ○ | 8.0 | ○ |
| Example 5 | R2 (60%) R3 (40%) | 2.0 | 0.5 | A1 0.5 | 47 | ⊚ | 8.1 | ○ |
| Example 6 | R2 (60%) R4 (40%) | 2.0 | 0.5 | A4 0.5 | 44 | ⊚ | 6.5 | ⊚ |
| Comparative Example 1 | R1 (60%) R3 (40%) | 5.0 | 1.0 | — | 112 | X | 13.8 | X |
| Comparative Example 2 | R1 (60%) R4 (40%) | 5.0 | 1.0 | — | 98 | X | 11.5 | Δ |
| Comparative Example 3 | R2 (60%) R3 (40%) | 2.0 | 1.0 | — | 78 | Δ | 9.2 | ○ |
| Comparative Example 4 | R2 (60%) R4 (40%) | 2.0 | 1.0 | — | 81 | Δ | 8.6 | ○ |
| Comparative Example 5 | R1 (60%) R3 (40%) | 2.0 | 1.0 | B1 0.5 | 73 | Δ | 8.2 | ○ |
| Comparative Example 6 | R1 (60%) R3 (40%) | 2.0 | 1.0 | B2 0.5 | 76 | Δ | 10.2 | ○ |

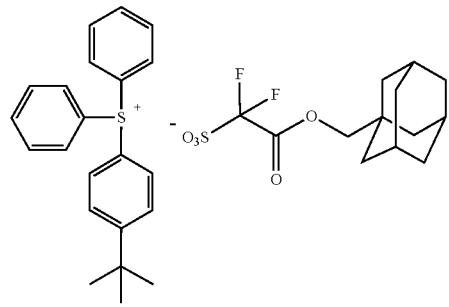

[Photoacid Generator]

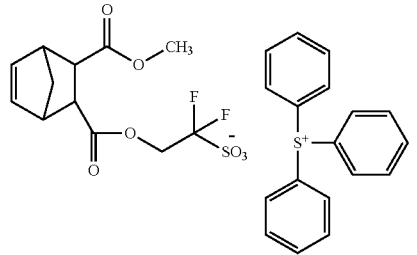

[compound B1]

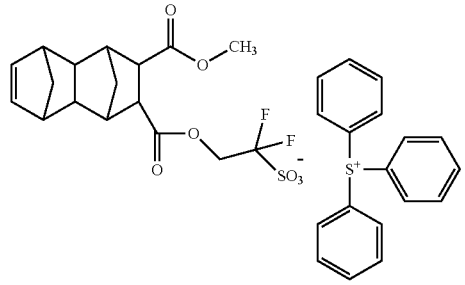

[compound B2]

In Table 2, the mass % of the photoacid generator, the quencher and the compound are based on 4% of the total resin solid content.

In Table 2, the photoresist evaluation condition was 120° C./60 s for SOB, 110° C./90 s for PEB, and 50 nm to 60 nm for the photoresist layer thickness.

Optimum exposure (dose): based on 32 nm pitch, it was described as 50 mJ/cm² or less (⊚), 70 mJ/cm² or less (○), 90 mJ/cm² or less (Δ), and greater than 90 mJ/cm² (X).

LWR (line width roughness): it was described as 7 nm or less (⊚), 10 nm or less (○), 13 nm or less (Δ), and greater than 13 nm (X).

As seen from Table 2, it was identified that the compound according to one embodiment of the present application was capable of, by having the structure of Chemical Formula 1, further enhancing contrast of an exposed portion and an unexposed portion in the photoresist process afterward, and was also capable of improving line width roughness (LWR) without reducing sensitivity.

According to Table 2, it was seen that Examples 1 to 6 were more useful for micropattern preparation compared to Comparative Examples 1 to 6 due to low dose. This is due to the fact that the photoresist composition used a photo-degradable base represented by Chemical Formula 1 having no sensitivity decrease caused by an increase in the base concentration, and as a result, a high resolution pattern was able to be obtained even with small exposure by having higher sensitivity compared to existing photoresist compositions.

In addition, according to Table 2, it was seen that Examples 1 to 6 were more useful for micropattern preparation compared to Comparative Examples 1 to 6 due to low line width roughness (LWR). It was due to high compatibility of the photo-degradable base, and it was identified that the compound was uniformly distributed into the photoresist composition improving LWR.

Furthermore, as seen in Examples 1 to 6, the compound according to one embodiment of the present application comprises a compound having $SO_3^-$ and $S^+$ ionic groups, and the photoresist layer was not able to be formed when the compound was not included since the function as a photoacid generator was not fulfilled.

The invention claimed is:

1. A compound represented by Chemical Formula 1:

[Chemical Formula 1]

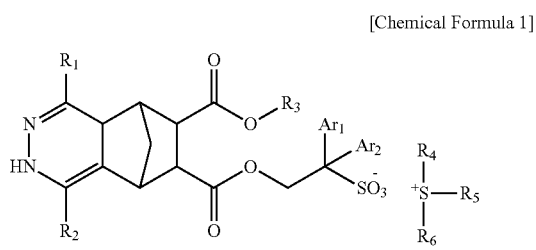

wherein, in the Chemical Formula 1, $R_1$ and $R_2$ are the same as or different from each other, and each independently hydrogen; a halogen group; a nitrile group; a hydroxyl group; an ester group; a substituted or unsubstituted alkyl group; a substituted or unsubstituted aryl group; or a substituted or unsubstituted heteroaryl group;

$R_3$ to $R_6$ are the same as or different from each other, and each independently hydrogen; a substituted or unsubstituted alkyl group; a substituted or unsubstituted cycloalkyl group; a substituted or unsubstituted alkoxy group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group; and $Ar_1$ and $Ar_2$ are the same as or different from each other, and each independently hydrogen; a halogen group; a substituted or unsubstituted alkyl group; or a substituted or unsubstituted aryl group.

2. The compound of claim 1, wherein $R_1$ and $R_2$ are the same as or different from each other, and each independently hydrogen; a halogen group; an ester group; a substituted or unsubstituted $C_1$ to $C_{60}$ alkyl group; a substituted or unsubstituted $C_6$ to $C_{60}$ aryl group; or a substituted or unsubstituted $C_2$ to $C_{60}$ heteroaryl group.

3. The compound of claim 1, wherein $R_4$ to $R_6$ are the same as or different from each other, and each independently a substituted or unsubstituted $C_6$ to $C_{60}$ aryl group.

4. The compound of claim 1, wherein $Ar_1$ and $Ar_2$ are the same as or different from each other, and each independently hydrogen; or a halogen group, and at least one of $Ar_1$ and $Ar_2$ is a halogen group.

5. The compound of claim 1, wherein $R_3$ is a substituted or unsubstituted $C_1$ to $C_{60}$ alkyl group.

6. The compound of claim 1, wherein the compound is represented by any one of the following Chemical Formulae:

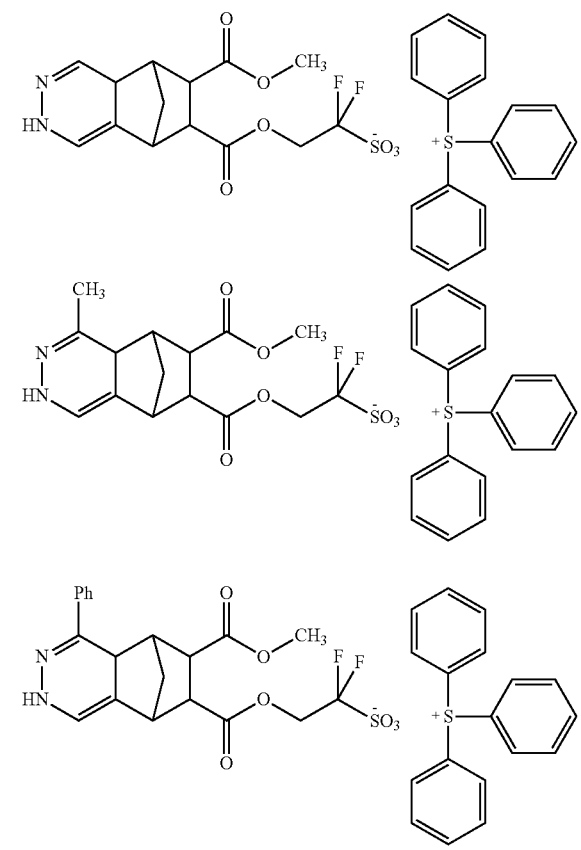

-continued

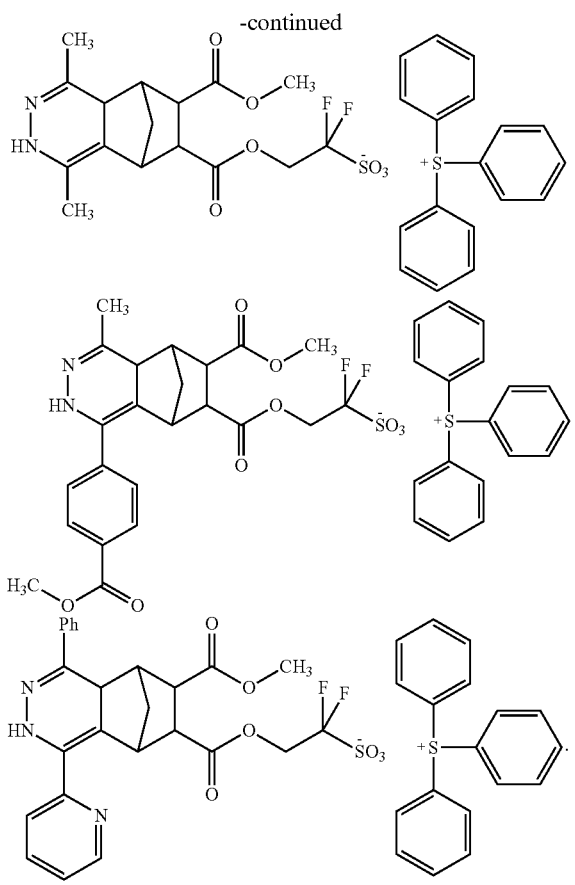

7. A photoresist composition comprising:
a resin;
the compound of claim 1;
a photoacid generator (PAG);
an acid diffusion control agent; and
a quencher.

8. The photoresist composition of claim 7, wherein the resin comprises at least one resin selected from a (meth) acrylate-based resin; a norbornene resin; a styrene-based resin; and an epoxy resin.

9. The photoresist composition of claim 7, comprising the compound in an amount of from 0.1 parts by weight to 20 parts by weight based on 100 parts by weight of the resin.

10. The photoresist composition of claim 7, comprising the photoacid generator in an amount of from 0.1 parts by weight to 20 parts by weight based on 100 parts by weight of the resin.

11. The photoresist composition of claim 7, comprising the acid diffusion control agent in an amount of from 0.1 parts by weight to 20 parts by weight based on 100 parts by weight of the resin.

12. The photoresist composition of claim 7, further comprising at least one material selected from a surfactant; a photosensitizer; and a photobase generator.

13. A photoresist layer comprising the photoresist composition of claim 7.

14. A method for preparing a photoresist pattern, the method comprising:
forming a photoresist layer by coating the photoresist composition of claim 7 on a semiconductor substrate;
selectively exposing the photoresist layer to ultraviolet rays; and
developing the exposed photoresist layer in a developing solution.

15. The method for preparing a photoresist pattern of claim 14, wherein the selectively exposing of the photoresist layer is aligning a mask on the photoresist layer, and exposing an area of the photoresist layer not covered by the mask to the ultraviolet rays.

16. The method for preparing a photoresist pattern of claim 14, wherein the developing of the exposed photoresist layer is removing the exposed portion in the photoresist layer by immersing in the developing solution.

* * * * *